United States Patent [19]
Lundquist

[11] 3,976,068
[45] Aug. 24, 1976

[54] DRUG DISPENSER FOR USE WITH INTRAVENOUS FEEDING PUMP

[75] Inventor: Ingemar H. Lundquist, Oakland, Calif.

[73] Assignee: Origo, Inc., Hayward, Calif.

[22] Filed: Jan. 3, 1975

[21] Appl. No.: 538,372

[52] U.S. Cl................................ 128/214 R; 128/272
[51] Int. Cl.²............................................ A61M 5/14
[58] Field of Search......... 128/214 R, 214 C, 214.2, 128/215, 218 R, 218 P, 218 G, 218 M, 220, 234, 238, 276, 278, 272

[56] References Cited
UNITED STATES PATENTS

| | | | |
|---|---|---|---|
| 1,410,530 | 3/1922 | Larche | 128/220 |
| 3,345,986 | 10/1967 | Roberts et al. | 128/214 R |
| 3,348,546 | 10/1967 | Roberts et al. | 128/218 M |
| 3,776,229 | 12/1973 | McPhee | 128/214 C |

FOREIGN PATENTS OR APPLICATIONS

| | | | |
|---|---|---|---|
| 705,392 | 3/1954 | United Kingdom | 128/218 M |

*Primary Examiner*—Dalton L. Truluck
*Attorney, Agent, or Firm*—Flehr, Hohbach, Test, Albritton & Herbert

[57] ABSTRACT

This invention relates to a drug dispensing capsule in which the drug may be first mixed with a predetermined quantity of parenteral fluid (the solution to be administered to the patient). It is adapted to be used at the discharge end of an intravenous feeding pump and will automatically switch over to the parenteral fluid as soon as the drug dosage has been dispensed. The device comprises a cylindrical chamber somewhat of the nature of an enlarged hypodermic syringe. It has an inlet at one end and an outlet at the other. A piston-like fluid separator is slidably mounted on the interior of said cylindrical chamber. The drug mixture to be administered is placed in the chamber between the piston and the discharge end of the chamber. The capsule is placed in the pumping system at the discharge end of the pump, the outlet from the device being connected to the tube to the needle inserted in the blood vessel of a patient. When the pump is operated, it pushes the piston axially in the cylinder thereby forcing the drug dosage out of the outlet end of the chamber and into the patient. When the piston reaches the end of the cylinder, the seal between the piston and the wall of the chamber is automatically broken, as by means of ridges projecting inwardly from the wall of the chamber, or by cavities formed in the wall thereof. Means is provided for exhausting air from the chamber, both when the parenteral fluid is introduced into the chamber and when a capsule with its premeasured dosage is placed in the system.

10 Claims, 4 Drawing Figures

U.S. Patent   Aug. 24, 1976   3,976,068
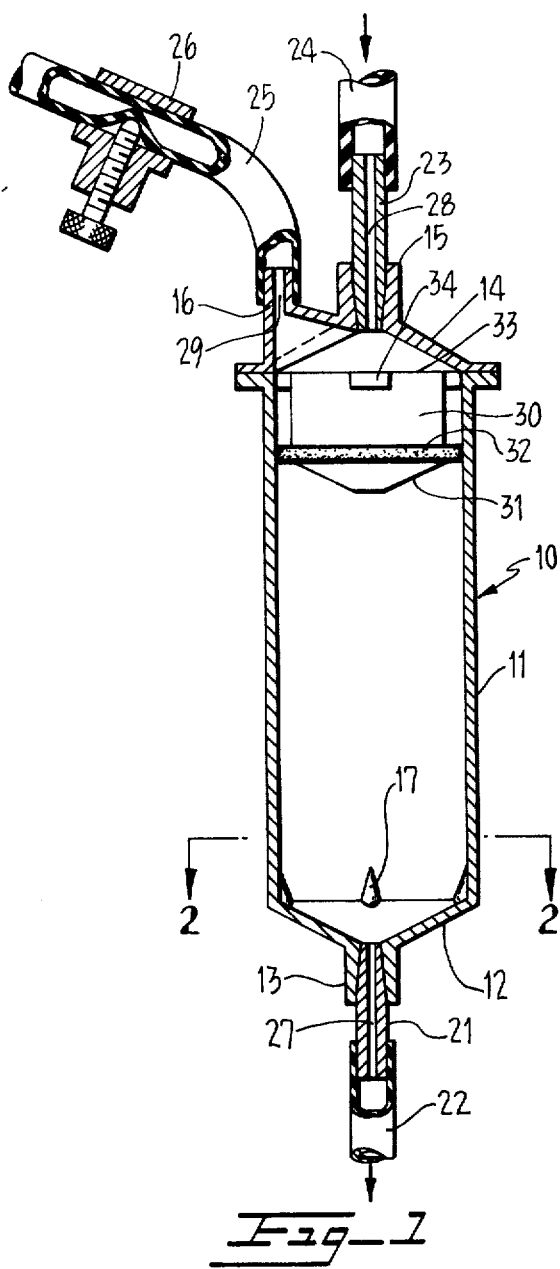
Fig_1
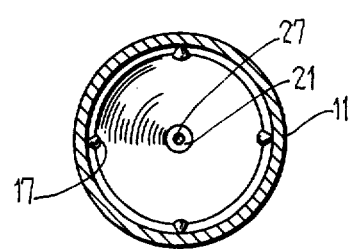
Fig_2
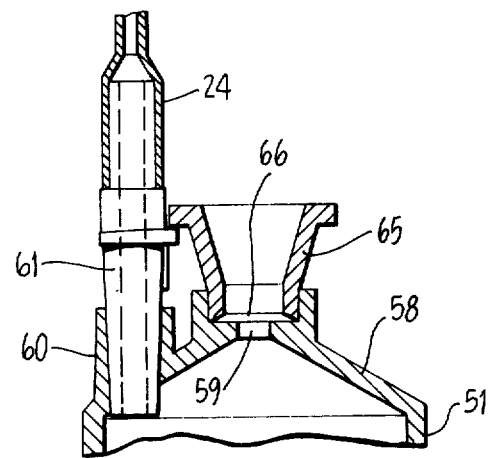
Fig_3
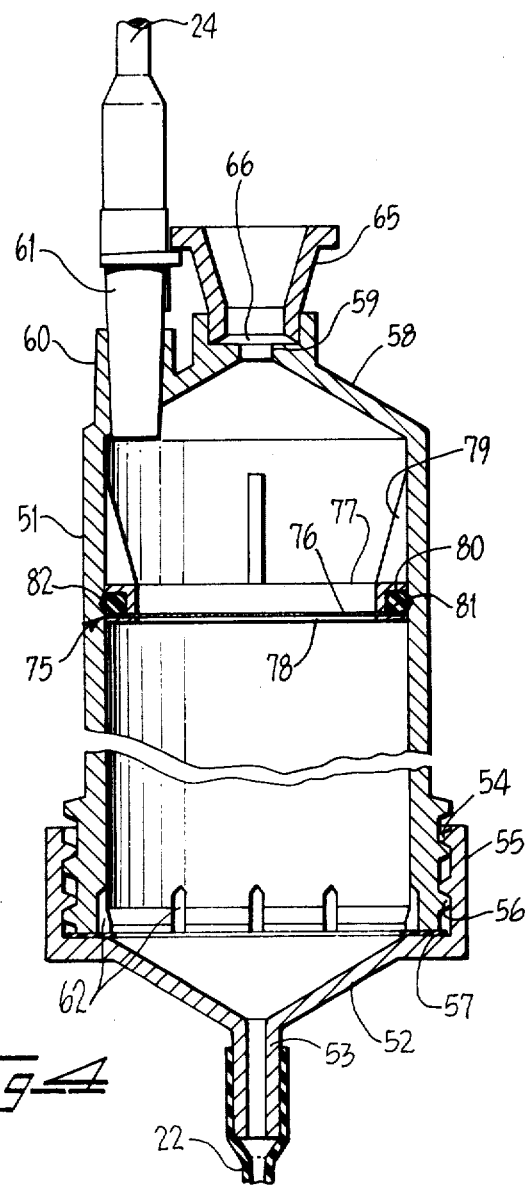
Fig_4

DRUG DISPENSER FOR USE WITH INTRAVENOUS FEEDING PUMP

BACKGROUND OF THE INVENTION

In recent years there has been great effort expended by researchers in a medical field for developing an intravenous feeding pump adapted to accurately measure and positively pump parenteral solutions from a supply container into the veins of a patient without having to rely upon the force of gravity alone. Such pumps have many advantages in administering the parenteral fluid and many designs have been suggested, including two covered by patent applications of this applicant, namely, Ser. No. 431,753, filed Jan. 8, 1974 now U.S. Pat. No. 3,874,826, and Serial No. 488,580, filed July 15, 1974.

Doctors often desire to introduce drugs into the blood stream of a patient, and whenever the patient is being fed intravenously, it is usually desirable to introduce the drug through the intravenous feeding system, as by injecting into the delivery tube to the patient. Quite often the drug is of such a character that it is advisable to dilute the drug in some predetermined ratio with the volume of solution being fed to the patient. The present device is directed to that end and provides a means whereby a desired volume of drug can first be diluted in a variable volume of the parenteral solution and then fed to the patient if that is desired. Then, as soon as the drug has been administered, it is usually desirable to return to the feeding of the parenteral solution. The necessary changes of course must be done with a minimum of contamination of the drug or the solution from contact with the air during the various steps of the process, and great care must be taken to prevent the feeding of air into the blood stream of the patient.

The device of the present invention is adapted to enable a hospital staff to use premeasured doses of a prescribed medication (prepared either by a drug manufacturer or by a hospital pharmacy in advance); to encapsulate the dosage into a suitable capsule which can readily be inserted into the intravenous feeding system with a minimum chance for contamination; and then to return to the feed of the parenteral solution without breaking the connection between the supply container of parenteral fluid and the needle which is inserted into the blood vessel of the patient. It is particularly adapted to be used in cooperation with an intravenous feeding pump, such as the ones suggested by the applicant's aforementioned patent applications, or any of the other intravenous feeding pumps which have been designed for this purpose.

OBJECTS

It is an object of the present invention to provide a capsule for a premeasured dosage of a drug (which may or may not be mixed with a measured amount of parenteral fluid) for inserting in an intravenous feeding line for injection into a patient.

It is another object of the invention to provide a drug mixing device adapted to mix a measured volume of drug and a measured volume of parenteral fluid for intravenous feeding into a patient in cooperation with a positive feed from the force of an intravenous delivery pump.

It is another object of the invention to provide a device for delivering a measured volume of drug (and, if desired, a measured volume of intravenous feeding fluid) for administration to a patient which avoids all possibility of contamination from air, and which does not require any change of the intravenous feeding needle or any part of the supply system after the drug has been administered.

A further object of the present invention is to provide means for the convenient and safe removal of air in a drug capsule. In one form the removal of air can be automatic.

A still further object of the present invention is to provide a drug dispenser for use with an intravenous delivery pump which can be filled with a predetermined dosage of drug mixed with a predetermined amount of base parenteral fluid which can be prepared at a remote point, such as by a drug manufacturer or a hospital pharmacy, and which, when the drug dosage is exhausted, will automatically switch over to a feed from the base fluid provided by the pump.

It is a further object of the invention to provide a capsule of premeasured drug dosage which can be inserted into an intravenous feeding system behind a positively operating pump and using the force of the pumped intravenous feeding to force the drug from the capsule; and then automatically restore feeding of the regular feeding solution.

These and further objects of the invention will be apparent from a disclosure which follows taken in conjunction with the drawing in which:

DRAWINGS

FIG. 1 is an enlarged cross-sectional view, on an enlarged scale, of one preferred form of the device of the present invention;

FIG. 2 is a plan view of the outlet end of the device shown in FIG. 1, such as taken on the plane indicated by the line 2—2 of FIG. 1;

FIG. 3 is a cross-sectional view on an enlarged scale of a second embodiment of the inlet end of the invention as shown in FIG. 1; and FIG. 4 is a partial, cross-sectional view, on an enlarged scale of another embodiment of the invention.

SPECIFICATION

The drug dispensing device 10 of FIG. 1 of the present invention comprises a cylindrical chamber, or capsule, 11, one end, such as 12, being formed integrally therewith. The integral end 12 preferably is of conical shape, as shown, in order to insure complete draining even if the capsule is not hanging in a truly vertical position. The conical end merges into an outlet nipple 13. The other, or inlet end of the cylindrical chamber 11 is closed by a cover plate 14, also preferably of conical shape. The cover 14 likewise merges into a nipple 15 which serves as the inlet into the chamber. The inlet cap 14 is also provided with a second nipple 16 leading from the utmost section of the capsule when the device is held in the vertical position shown in FIG. 1, which nipple serves as an air outlet. This form of the device is provided with a series of disengaging wedges 17 at the outlet end of the chamber 11 which are effective to break the seal of a piston-like fluid separator with the wall of the chamber, which piston normally has a sealing engagement with the wall of the chamber and is pushed to the outlet end 12, as will hereinafter be described. The cap 14 is adapted to be sealed to the cylindrical chamber 11 by any suitable means, such as electronic welding, cementing by a suitable cement, or the like.

A short rigid adapter outlet 21 provided with a central bore 27 is adapted to be inserted into the nipple 13 and to be inserted at its other end into a discharge tube 22, as shown in FIG. 1. This discharge tube 22 leads to the intravenous feeding needle (not shown) which is inserted into the blood vessel of a patient needing intravenous feeding. The needle is not shown herein as it is of conventional construction and, while used with the invention herein, is not a part of the invention.

A short inlet adapter 23 is adapted to be inserted into the bore of nipple 15 at the inlet end of the chamber 11, and is provided with a central bore 28 as shown. The other end of this insert 23 is adapted to be inserted into a delivery tube 24 leading from an intravenous feeding pump (not shown), such as those mentioned in the copending applications heretofore mentioned.

Similarly, the nipple 16 is provided with a central bore 29 and is adapted to be embraced by a short length of tube 25 which will be equipped with a sealing clamp 26.

Inside the chamber 11 is a piston 30, the outlet side 31 of which is conical in shape adapted to compliment, or fit, the angle of the discharge end 12 of the cylinder, so that when the piston is in its lowermost position (which does not quite engage the end 12 of the chamber) there will be little space between the two. This piston is provided with a soft resilient sealing ring 32 and with a series of guide members 34 which prevent cocking of the piston in the cylinder 11. The top surface 33 of the piston 39 can be of any configuration, such as flat, as shown in FIG. 1.

Whenever it is desired to administer a drug to a patient, or a mixture of drug and carrying fluid (such as the parenteral fluid normally fed to such a patient), the capsule is inverted and the drug dosage is inserted into the chamber 11 by any suitable means through the nipple 13 in the outlet end 12. At this stage the clamp 26 is opened so that all air can escape from the inlet side of the piston while the inlet itself will be sealed by some suitable means, not shown. The carrier, or parenteral fluid, is then inserted into the same space. Such injection of drug and parenteral fluid will force the piston 30 upwardly in the cylinder 11. After the drug and its carrier is inserted in the chamber 11, the outlet end and the air valve are also sealed until it is desired to administer the same to the patient. At the latter time, the air valve clamp 26 will be released and the closure of the inlet end of the device will be removed and the same connected to the discharge tube 24 leading from the intravenous feeding pump. Fluid will then be pumped into the upper chamber until it flows through the air vent and pumping will then be stopped and the air vent closed by the closing of the clamp 26. At this point the sealing device used to close the outlet end of the dispensing device will be removed and operation of the pump is resumed so as to force the piston toward the outlet end and thus force all of the air out of the outlet end of the capsule. As soon as the drug dosage overflows the outlet 13 or adapter 21, as the case may be, the pump is stopped and this end is immediately connected to the discharge tube 22 leading to the patient. By the means herein described, no air will be present in the chamber 11, at the start of pump operation, so that none can be pumped to the blood stream of the patient. The capsule 10 is again inverted and the pump is then restarted. As the pump operates, it pumps fluid through the tube 24, and insert 23 into the upper section of the chamber formed between the cylinder 11 and the cap 14. Such pumping forces the piston downwardly and that, in turn, forces the drug dosage out of the lower section of the chamber 11 into the outlet insert 21 and delivery tube 22. It will be understood that the fluid being pumped will pass by the guides 34 at the upper section of the piston 30 and will rest against the sealing ring 32 while the drug dosage will be on the opposite face of the sealing ring 32. When the piston 30 reaches the lower section of the chamber 11, the sealing ring 32 engages the wedges 17, thereby breaking the seal of the sealing ring 32 with the wall of the cylinder 11 and permitting the passage of parenteral fluid through the upper section of the chamber by the sealing ring 32 and into the outlet tube 22. Thus, the feeding of the base parenteral fluid will automatically continue after the drug dosage has been administered. It will be understood that the drug dosage can be previously prepared as in the hospital pharmacy or even in a drug manufacturing house, whereupon it will be sealed against contamination and it will be ready for usage when desired.

It will also be understood that such device need not be removed from the feeding conduits with consequent danger of contamination or the entry of air into the system. It need only be replaced when it is next required to administer a drug to the patient.

A second form of air valve is shown in FIG. 3. In this embodiment the air relief means comprises a cap member 65 adapted to be firmly set into the upper end of the inlet cap 58, such as by a press fit or cementing. At its inner end the cap 65 is provided with an air exhaust filter 66 of the hydrophobic type, that is, one which lets air pass but does not permit fluid to pass. These filters are operative at pressures greatly in excess of that supplied by an intravenous feeding pump so that there is no danger of loss of fluid through this filter. The pores of such a filter can be of such a size that bacteria cannot enter, so sterile conditions are preserved within the capsule. Thus, as the drug-carrier mixture is inserted into the open outlet end, the piston will be forced toward the inlet end and any air trapped between the piston 30 and the inlet end 58 can be exhausted through the filter 66, but when liquid is pumped into the drug dispenser, it can fill the upper part of the chamber but cannot escape therefrom.

Another embodiment of the present invention is shown in FIG. 4. It comprises a cylindrical chamber 51, one end 58 of which (in this case inlet end) is formed integral therewith. The integral inlet end 58 is preferably conically shaped to form a chamber with sloping sides to lead air to a central filtered air vent like that shown in FIG. 3. Thus, there is a centrally located aperture 59 in the conical inlet end 58. Eccentrically mounted therefrom is a fluid inlet 60 adapted to receive either the pump delivery tube 24 or an adapter 62 interposed between the tube 24 and the chamber within the cylinder 51. The aperture 59 is closed by a hydrophobic filter 66 held in place by a tightly fitting holder 65.

The outlet end of the end of the cylinder 51 is formed as a cap 52 provided with a central nipple 53 adapted to be inserted into the tube 22 which leads to the needle inserted in the blood vessel of a patient. In this form the cap 52 is threaded upon the outer wall of the cylinder 51 as by means of threads 54 formed on a vertical extension 55 of the interior wall of the cap 52, which engage threads 56 formed on the exterior wall of the cylinder 51. A gasket 57 is clamped between the end of the cylinder 51 and the base section of the cap 52, as shown in FIG. 3. The lower portion of the cylinder 51 is provided with a series of base fluid passage ports 62 as shown in this figure.

In this embodiment the piston 75 is shown as a flat member provided with a hydrophobic filter seal 76. The filter member 76 is clamped between a pair of annular rings 77 and 78 which are securely held together, as by cementing, rivets, or other means, not shown. The upper ring 77 is provided with several guide vanes 79 to keep the piston from tilting. Preferably the two rings 77, 78 are formed to provide a peripheral slot 80 into which can be placed a sealing O-ring 81. It is preferred to form a small circumferential depression 82 in the interior wall of the cylinder adjacent the inlet end, as shown. If the piston 75 is moved to this location at the time of the assembly of the capsule, the piston 75 will be held there when it later receives the drug dosage.

In the devices herein described, it is assumed that they will be loaded with a prescribed amount of drug either in a drug manufacturing facility or in a hospital pharmacy -- in both of which the maintenance of sterile conditions is possible and is also stressed. In this form of capsule, the capsule is inverted and the drug solution introduced through the outlet end of the cylinder 51 (the cap, of course, being removed). The cap 52 is then tightly screwed onto the cylinder and the device can then be thoroughly sterilized by any one of several known procedures and finally sealed in a sterile plastic bag. Thereafter, the capsule can be stored until needed.

Since the filters 66 and 76 are hydrophobic, they permit the passage of air but not water under conditions prevailing in an intravenous feeding system. For example, air will pass through them fairly readily under 1 p.s.i. pressure and liquid will not pass through until pressures in the neighborhood of 300 p.s.i. are reached. Since intravenous feeding pumps usually operate at pressures of 3 or 4 p.s.i., they provide sufficient pressure to force air through the filter but not enough to permit water to flow through. Thus, there is no danger of the drug solution passing through the piston 75 after the drug solution has been put into the capsule.

When the capsule is put into the intravenous feeding system, the outlet tube 22 will usually be sealed, as by a clamp, not shown in FIG. 4. The pump is then started, and will first fill the inlet chamber (between the piston 75 and the end wall 58), forcing the air out of that chamber until the liquid level reaches the air vent filter 66. Thereafter, the continued operation of the pump will force the piston 75 from its retaining depression 82 — at about 2 p.s.i. Continued operation of the pump moves the piston 75 downwardly in the cylinder until the body of drug solution is reached — any air in the outlet chamber (between the piston 75 and the outlet end 52 of the cylinder) passing first through filter 76, the body of fluid in the inlet chamber, and out of the system through air vent filter 66. The clamp, or other valve means, in the outlet tube 22 is then opened, and continued operation of the pump will force the liquid separator 76, 77, 78 toward the outlet, pushing the drug dosage ahead of it. As the drug solution is exhausted, the sealing O-ring 81 will come to the level of the outlet ports 62 and parenteral fluid from the pump can pass to tube 22 leading to the patient. Thus, after the drug has been administered, the feeding of the regular intravenous feeding solution is automatically resumed and the capsule does not have to be removed from the feed system.

This type of device can also be designed for use in an inverted position, in which case the inlet end 59 would be provided with an intravenous feeding inlet 60 as shown, but would not require the air vent formed of the cap 65 and hydrophobic filter 66. In this design, the air outlet 59 would be completely eliminated. In this design of the device, the capsule is designed to be inverted, so that the outlet end 53 is uppermost and the intravenous feeding fluid is pumped into the bottom of the container, the cylinder 51 hanging with the cap end 52 uppermost. When the pump is started, it will first fill the inlet chamber (between the piston 75 and end wall 58), forcing air out of the chamber through the intermediate hydrophobic filter 76 and bubbling it through the drug solution and out through the outlet 53. At this stage of operation, the outlet 53 must be open to atmosphere, as air must not be permitted to enter the bloodstream of the patient. Thereafter, the continued operation of the pump will force the piston 75 from its retaining depression 82 at about a pressure of 2 p.s.i. Continued operation of the pump moves the piston upwardly in the cylinder until the body of the drug solution reaches the outlet end, thereby pressing any air in that chamber ahead of it. Thus, when all the air is removed in the system, the needle can be inserted into the patient, or a needle already there can be attached to the outlet nipple 53. Thereafter, the administration of the drug is secured from the force of the pump at the desired rate. All air is thus removed from both sides of the separated piston filter.

It can be noted that with the use of capsules of the present invention, it is immaterial once the air is removed as to whether the capsule is suspended in the position shown or in an inverted position, or even a horizontal position. It will also be seen that once the connections of the capsule to the feeding line is completed and the air removed from the system, the system is "closed" (i.e., no air can contact the feeding solution) after it leaves the container of parenteral fluid.

It will be obvious to those skilled in the art that many forms of a disposable drug dispenser adapted for use with an intravenous feeding pump can be designed involving the principles herein shown and described. Since the preferred embodiments are shown, it is believed unnecessary to further describe the device.

What is claimed is:

1. A drug dispensing device for a patient adapted for use in conjunction with an intravenous feeding pump providing a source of parenteral fluid supplied aat a controlled rate comprising:
   a. a cylinder;
   b. means enclosing both ends of said cylinder;
   c. a liquid separator slidably fitting inside said cylinder and forming first and second chambers in said cylinder on opposite sides of said liquid separator;
   d. a fluid inlet into one end of said cylinder in continuous communication with said first chamber and adapted to be connected to said source of parenteral fluid;
   e. an outlet from the other end of said cylinder; and in continuous communication with said second chamber and adapted to be connected to the patient,
   f. a drug in a liquid carrier disposed in said second chamber;

g. means adjacent said outlet end of said cylinder for bypassing said liquid separator whereby upon introduction of parenteral fluid into said first chamber said liquid separator will be moved to cause said drug in a liquid carrier to be forced into the patient and thereafter parenteral fluid into the patient without breaking the connections between the source of parenteral fluid and the patient.

2. The device of claim 1 together with hydrophobic means carried by the liquid separator for permitting air to pass between said first and second chambers.

3. The device of claim 2 together with hydrophobic means carried by the cylinder for permitting air to escape from the cylinder.

4. The device of claim 1 wherein means for bypassing said liquid separator includes at least one channel formed in the inner surface of said cylinder and having a length which is greater than the thickness of the liquid separator.

5. The device of claim 1 wherein the means for bypassing said liquid separator includes at least one ridge carried by the inner surface of said cylinder adapted to deform said liquid separator and thereby provide a leakage path around said liquid separator.

6. The apparatus of claim 1 together with guide vanes carried by the liquid separator to prevent tilting of the liquid separator within the cylinder.

7. Apparatus for administering drugs and parenteral fluids to a patient, a source supplying parenteral fluid at a controlled rate, a container having inlet and outlet ends, means connecting the inlet end to the source of parenteral fluid, a piston-like member slidably disposed in said container forming first and second chambers in said container on opposite sides of said piston-like member with the first chamber being in continuous communication with the inlet end and the second chamber being in continuous communication with the outlet end, said piston-like member forming a liquid tight seal between said first and second chambers, parenteral fluid from said source filling said first chamber, a drug in a liquid carrier filling said second chamber, means for connecting the outlet end to the patient, means carried by the container adjacent to the outlet end of the container for bypassing the piston-like member whereby upon introduction of additional parenteral fluid into the first chamber, the piston-like member is caused to move to force the drug in the liquid carrier into the patient and thereafter parenteral fluid into the patient without breaking the connections between the source of parenteral fluid and the patient.

8. Apparatus as in claim 7, together with hydrophobic means carried by the piston-like member to permit air to pass through said piston-like member from one of said chambers to the other of said chambers.

9. Apparatus as in claim 8, together with means for permitting escape of air from said container.

10. In a method for administering drugs and parenteral fluids to a patient by the use of a container having inlet and outlet ends with the outlet end being adapted to be connected to the patient and the inlet end adapted to be connected to a source of parenteral fluid and with a piston-like member slidably mounted within the container and serving to form first and second liquid-tight chambers in the container on opposite sides of the piston-like member with the first of the chambers being in continuous communication with the inlet end and the second of the chambers in continuous communication with the outlet end, the steps of placing a drug to be administered to a patient in a liquid carrier in the second chamber, introducing parenteral fluid into the first chamber to move the piston-like member in the container to force the drug from the second chamber into the patient and thereafter introducing parenteral fluid into the patient by causing the parenteral fluid to bypass the piston-like member after the drug has been supplied to the patient without disturbing the connections to the patient and to the source of parenteral fluid.

* * * * *